United States Patent [19]

Nagji et al.

[11] Patent Number: 4,876,394

[45] Date of Patent: Oct. 24, 1989

[54] PROCESS FOR THE PRODUCTION OF METHYL TERT.-ALKYL ETHERS

[75] Inventors: Moez M. Nagji, Stamford, Conn.; Robert E. Trubac, Ridgewood, N.J.

[73] Assignee: UOP, Des Plaines, Ill.

[21] Appl. No.: 213,238

[22] Filed: Jun. 29, 1988

Related U.S. Application Data

[63] Continuation-in-part of Ser. No. 204,301, Jun. 9, 1988, Pat. No. 4,814,517.

[51] Int. Cl.$^4$ .............................................. C07L 41/06
[52] U.S. Cl. .................................................... 568/697
[58] Field of Search ........................................ 568/697

[56] References Cited

U.S. PATENT DOCUMENTS 4,447,653 5/1984 Vora ...................................... 568/697

Primary Examiner—Howard T. Mars

Attorney, Agent, or Firm—Thomas K. McBride

[57] ABSTRACT

In the production of methyl tert.-alkyl ethers by the reaction of methanol with isoalkylenes, the formation of dimethyl ether as an undesirable reaction by-product is reduced by recycling dimethyl ether to the reactor, advantageously in amounts sufficient to establish an equilibrium between the amount of dimethyl ether imparted to the reactor by way of recycle and the amount of dimethyl ether leaving the reactor as a portion of the reaction product whereby the formation of dimethyl ether in the reactor is essentially nil. In the present invention the essential recycle of dimethyl ether is accomplished by providing an adsorption capacity for dimethyl ether in the adsorption unit for recovering unreacted methanol and recycling dimethyl ether in combination with recycled methanol to the reactor as an effluent from the methanol adsorption unit during regeneration with isobutylene-containing C$_4$ hydrocarbon feedstock.

6 Claims, 1 Drawing Sheet

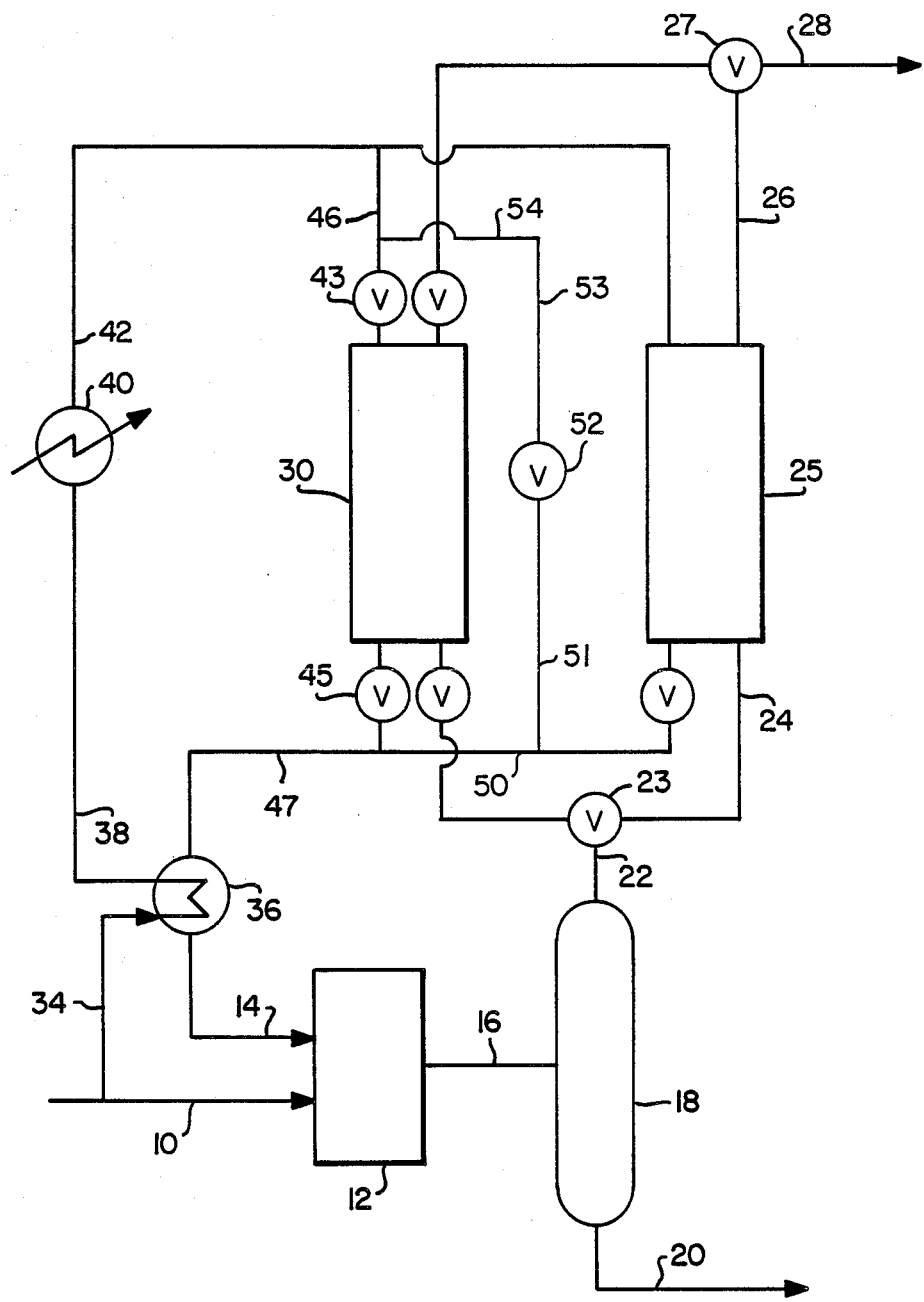

PROCESS FOR THE PRODUCTION OF METHYL TERT.-ALKYL ETHERS

This application is a continuation-in-part of copending application Ser. No. 204,301 filed June 9, 1988, now U.S. Pat. No. 4,814,517, the entire disclosure of which is incorporated herein by reference.

The present invention relates to a process for the production of ethers by the reaction of an alcohol with an isoolefin. The invention more particularly relates to the preparation of methyl tert.-butyl ether and methyl tert.-amyl ether by the reaction of methanol with isobutylene and isoamylene respectively. The invention specifically relates to the reduction in the amount of dimethyl ether formed as a reaction by-product by means of adsorption of at least a portion of the by-product dimethyl ether in the same adsorption system used to recover unreacted methanol and recycling the dimethyl ether and methanol back to the reactor.

BACKGROUND OF THE INVENTION

The production of ethers by the reaction of an isoolefin and an alcohol is a well-known commercial operation. A number of detailed descriptions of such processes, particularly as they relate to the production of methyl tert.-butyl ether (MTBE) and methyl tert.-amyl ether (MTAE) are disclosed in the prior art. These ethers are useful as high octane blending agents for gasoline motor fuels by virtue of their high Research Octane Number (RON) of about 120. Perhaps the most commonly employed reaction in the preparation of MTBE and MTAE is that between methanol and isobutylene or isoamylene, respectively. A wide variety of catalyst materials have been found to promote this reaction including ion-exchange resins such as divinylbenzene cross-linked polystyrene ion exchange resins in which the active sites are sulfuric acid groups; and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of methanol and isobutylene.

The preference for the isoalkylene-methanol reaction is in part, at least, due to the relative abundance of the starting materials. Both isobutylene and isoamylene are readily available in a petroleum refinery from both fluid catalytic crackers and as a by-product of ethylene production. Methanol is, of course, a staple commercial chemical of long standing. Moreover, isobutylene, because of its volatility, cannot be added to the gasoline pool without alkylation. Methanol cannot be added to qasoline in significant quantities because of immiscibility problems and because of its corrosiveness toward existing internal combustion engines. The combining of these two compounds thus appears to be an advantageous way to extend the gasoline pool. The modification of a gasoline by the conversion of 2-methyl-1-butene and 2-methyl-2-butene to methyl tert.-amyl ether is proposed in U.S. Pat. No. 3,482,952.

In addition to being useful in the preparation of high octane ethers for gasoline up grading, the etherification process is also useful as a separation process. The reaction of methanol with mixed $C_4$ and $C_5$ olefins is selective for the isobutylene and isoamylene isomers. Therefore, a mixed butylene and/or amylene stream common to refineries can use the aforesaid etherification process to separate this mixture and to produce a stream of essentially pure normal butenes and/or amylenes and essentially pure MTBE and/or MTAE. The ethers can subsequently be cracked to produce essentially pure isoalkylenes.

A wide variety of reaction conditions have heretofore been proposed for carrying out the reaction of isobutylene or isoamylene with methanol, depending in part upon the type of catalyst employed in each case. Thus, both vapor phase and liquid phase processes are known in which reaction temperatures are from about 50° C. to about 400° C., pressures vary from atmospheric to 1,500 psig, and the mole ratios of methanol to isoalkylene range from 0.1:1.0 to about 10:1. Both batch type and continuous process schemes are said to be suitably employed.

It is commonly the case that the source of isobutylene is a mixed $C_4$ hydrocarbon stream from a refinery operation, and the reaction with methanol is carried out in the liquid phase at a temperature not exceeding 100° C. The quantity of the MTBE produced depends upon the isobutylene content of the $C_4$ hydrocarbon stream used. When a $C_4$ hydrocarbon stream cut from steam cracking is used, providing a feedstock with approximately 50% isobutylene after butadiene extraction, the reactor effluent can contain almost 60% MTBE and can sometimes be used as a gasoline component without further treating. It is generally more desirable, however, to separate the unreacted $C_4$'s from the reactor effluent by distilling off the unconverted $C_4$'s. When this is done, MTBE of about 98% purity can be produced at an isobutylene conversion of about 95%. A further increase in the conversion, based on isobutylene, can be achieved only by usinq a higher methanol/isobutylene ratio in the reactor feedstock. Because greater than stoichiometric amounts of methanol are used in the high conversion MTBE processes (also to allow for fluctuating isobutylene concentrations), additional steps have to be included in such processes to recover the excess methanol from reactor effluent. The recovered methanol is then recycled to the reactor feed stream.

In the MTBE reactor, one of the more significant side reactions which occurs is the dehydration of methanol to form dimethyl ether. The formation of dimethyl ether is particularly undesirable since it is a detrimental catalyst poison in down stream processing of any unreacted hydrocarbons, such as normal $C_4$-$C_5$ olefins and $C_4$-$C_5$ paraffins, which are present in the hydrocarbon feed to the MTBE reactor.

It has heretofore been proposed to treat the effluent from the MTBE reactor in fractionation column and recovering the MTBE as the bottoms product. The light hydrocarbons, methanol and dimethyl ether are recovered as the column overhead and then passed through a first adsorption system to selectively adsorb the methanol and thence through a second adsorption system to isolate the dimethyl ether. The methanol adsorption system is regenerated, advantageously using a purge stream which is the intended hydrocarbon feed for the MTBE reactor, and the effluent methanol-containing hydrocarbon stream recycled to the MTBE reactor. The dimethyl ether adsorption system is regenerated by purge desorption and the effluent purge stream vented from the system for disposal or other treatment.

STATEMENT OF THE INVENTION

It has now been found that the make of dimethyl ether (hereinafter "DME") in the MTBE reactor can be appreciably reduced by recycling at least some of the DME in the reactor effluent back to the reactor whereby the equilibrium of methanol dehydration reaction:

$$2CH_3OH \rightarrow CH_3-O-CH_3 + H_2O$$

is shifted toward the left, thus decreasing the formation of additional DME. More particularly, it had been found that by increasing the capacity of the adsorbent in the methanol recovery system for the adsorption of DME, upon regeneration of the adsorbent with a portion of the hydrocarbon feed to the MTBE reactor and recycle of the recovered methanol back to the reactor, DME is also desorbed and recycled to the reactor. In due course the recycled DME builds up in the reactor-fractionation column loop until the concentration of DME in the feed to the methanol adsorption system exceeds the capacity of the adsorbent for DME. An equilibrium is reached whereby the amount of unadsorbed DME leaving the methanol recovery adsorption bed is equal to the amount of DME formed in the MTBE reactor. The unadsorbed DME from the methanol recovery adsorption bed is removed from the effluent hydrocarbon stream using an additional adsorption system in order to sufficiently purify the hydrocarbons for subsequent alkylation or hydrogenation process.

Accordingly, the present invention resides in the cyclic process for preparing methyl tert.-alkyl ether which comprises the steps of (a) contacting and reacting in a reaction zone and in the liquid phase a reaction mixture formed by combining a stream consisting essentially of hydrocarbons having from 4 to 5 carbon atoms and containing at least some proportion of an isoalkylene having from 4 to 5 carbon atoms with methanol to form a reaction product comprising methyl tert.-alkyl ether, at least 50 ppm (w) unreacted methanol, unreacted $C_4$-$C_5$ hydrocarbons and at least 5 ppm (w) dimethyl ether;

(b) isolating at least 99 percent (v) of the methyltert.-alkyl ether from the reaction product;

(c) treating the residual portion of the reaction product containing both dimethyl ether and methanol by passing said residual portion through a first adsorption zone containing an adsorbent for both methanol and dimethyl ether whereby at least 95 weight percent preferably 98 weight percent, of the methanol present in adsorbed and the weight ratio of adsorbed dimethyl ether to adsorbed methanol is at least 0.01, preferably at least 0.10, and more preferably from 0.20 to 0.50; and a substantially methanol-free effluent is obtained which comprises non-adsorbed $C_4$-$C_5$ hydrocarbons and dimethyl ether;

(d) passing the effluent from step (c) through a second adsorption zone containing a selective adsorbent for dimethyl ether and recovering a hydrocarbon effluent dimethyl ether content, preferably a substantially pure hydrocarbon effluent;

(e) periodically regenerating the first adsorption zone by passing therethrough a non-sorbable purge fluid, preferably a $C_4$-$C_5$ hydrocarbon stream of essentially the same composition as the hydrocarbon stream fed to the reactor in step (a) and recycling the desorbed methanol and dimethyl ether to the said reaction zone;

(f) repeating the process of step (a) to produce additional methyl tert.-alkyl ether and a reduced proportion of dimethyl ether with respect to the initial reaction in said reaction zone.

BRIEF DESCRIPTION OF THE DRAWINGS

This sole FIGURE of the drawings is a schematic flow diagram of an adsorption system suitable for the practice of the present invention.

DETAILED DESCRIPTION OF THE INVENTION

The following description of the present process with respect to the production of MTBE is made with reference to the flow diagram of the drawings. In the interest of simplifying the description of the invention, the process system in the drawing does not contain the several conduits, valves and the like which in actual practice would be provided in accordance with routine skill in the art to enable the process to be carried out continuously.

Methanol in the liquid phase enters the reaction system through line 10 and enters the reactor 12 along with a $C_4$ hydrocarbon liquid stream comprising isobutylene entering through line 14. Advantageously, all fluid streams introduced into the system have previously been dried to a water dew point of 0° C. to 10° C. at the operating pressure of the reactor. Reactor 12 is operated at a temperature which in large measure is dependent upon the particular catalyst employed but is generally in the range of about 40° C. to 90° C. and using an internal system pressure sufficient to maintain the reaction mixture in the liquid phase. In the present embodiment, the catalyst is of the ion-exchange resin type and the temperature of the reactor is about 60° C. The isobutylene-containing $C_4$ hydrocarbons including butene-1, cis and trans butene-2, butadiene, isobutane and n-butane along with the isobutylene. Preferably the isobutylene is present in an amount of at least 10 mol-%. The molar ratio of methanol to isobutylene is less than 1.0. The effluent from the reactor comprises product MTBE, unreacted methanol, unreacted $C_4$'s and dimethyl ether in addition to other reaction by-products. This effluent is passed through line 16 to distillation unit 18. While in this illustration the reactor and distillation tower are represented as two separate apparatuses, relatively recent advances have made possible the combination of the function of the reactor and the distillation tower into a single piece of apparatus. For purposes of the present invention, either operational mode is suitably employed. As a result of the distillation process, MTBE product is recovered from the bottom and is removed from the system through line 20. The overhead effluent from the distillation tower comprises from about 4000 ppm (w) unreacted methanol, unreacted $C_4$ hydrocarbons, 200 to 2500 ppm (w) dimethyl ether as well as trace amounts of other volatile by-products. This effluent passes through line 22, valve 23 and line 24 to compound adsorbent bed 25 containing in the ingress (bottom) end a commercially available silica gel adsorbent and in the egress (top) end zeolite 13X (sodium zeolite X). The temperature within the adsorption bed is preferably at an initial temperature of from 30° C. to 50° C. The effluent from the distillation unit 18 is at a temperature of from about 30° C. to 50° C. and enters bed 25 without being cooled. The pressure in bed 25 is maintained such as to cause the dimethyl ether and methanol-containing $C_4$ fluid stream being treated therein to be in the liquid phase. The initial effluent from bed 25 contains from about 0 to 100 ppm(w) methanol and about 0 to 2500 ppm(w) dimethyl ether, with the balance being principally a mixture of olefinic and saturated n-$C_4$ hydrocarbons. This effluent is passed through line 26, valve 27 and line 28 and can be removed from the process system with or without further treatment to remove additional dimethyl ether and utilized as feed for an alkylation unit. While the adsorption step is being carried out in bed 25, bed 30, which is essentially identical with bed 25 insofar as configuration and loading with silica gel and zeolite 13X is concerned, is being regenerated after previous service in methanol and dimethyl ether removal from the raffinate from distillation unit 18. The regeneration of bed 30 is accomplished in the conventional manner by purging in a direction countercurrent to the direction of flow through the bed during the adsorption step therein, using a portion of the same hydrocarbon feed stream being fed to reactor 12 through line 10. The hydrocarbon regeneration stream enters the system through line 34 and passes through heat-exchanger 36, line 38 and heater 40 wherein its temperature is raised to the range of at least 50° C. (122° F.) preferably at least about 80° C. (176° F.) up to about 121° C. (250° F.). Preferably the temperature of the purge stream is from about 80° C. to about 115° C. The pressure conditions are controlled to maintain the $C_4$ hydrocarbon stream through bed 30 substantially in the liquid phase. From heater 40 the hydrocarbon stream is passed through lines 42 and 46 and valve 43 into adsorbent bed 30. The effluent desorbed methanol, dimethyl ether and $C_4$ purge stream from bed 30 are, depending upon the temperature of the entering purge stream, either passed in its entirety through valve 45 and line 47 to heat exchanger 36, or some portion thereof is recycled to the ingress end of bed 30 through lines 50 and 51, valve 52, lines 53 and 54 and valve 43. If the temperature of the purge stream entering bed 30 from heater 40 through line 42 and valve 43 is at a temperature greater than about 115° C., the volume of purge fluid will, in normal practice, be sufficient to regenerate bed 30 to the required degree using a single pass through the bed. At lower temperatures, however, recycle of a portion of the purge will be required—the proportion being dependent upon the existing temperature of the purge stream. Optionally, the recycled bed effluent can be reheated prior to being admixed with fresh purge from line 42. Regardless of the regeneration mode employed, the effluent from bed 30 eventually is all passed via line 47 through heat exchanger 36 wherein its temperature is decreased to about 60° C. to 95° C., i.e., a temperature suitable for operation of the reactor 12, to which it is passed via line 14. The purge regeneration of bed 30 is continued until desired level of residual methanol and dimethyl ether is achieved. It is important that the capacity of the adsorbent bed for dimethyl ether be maintained since a buildup of concentration of dimethyl ether in the reactor-adsorber loop is necessary in order to establish the equilibrium in which the total of the DME passing through beds 25 and 30 during the adsorption step therein is essentially the same as the DME being produced in reactor 12, and lower than would be made if there were no DME adsorption on bed 25 or bed 30. At this point adsorption bed 25 is at the end of the adsorption stage in its operation and is ready to be regenerated as described hereinabove with respect to bed 30.

While the process of the present invention has been illustrated hereinabove using as the adsorbent for the methanol and dimethyl ether a compound bed of silica gel and zeolite 13X it will be understood by those skilled in the art that any of the well known adsorbents for these compounds can be employed whether in simple or in compound or in dual beds, provided only that there exist and be maintained a capacity for adsorbing essentially all of the methanol and a sufficient proportion of the dimethyl ether from the fractionation column overhead to reduce the DME make in the MTBE reactor to the desired degree.

Also, although the present invention has been illustrated hereinabove with reference to $C_4$ hydrocarbon streams and isobutylene, it will be understood that the descriptions are equally applicable to the production of methyl tert.-amyl ether using isoamylene and $C_5$ hydrocarbon streams.

What is claimed is:

1. A cyclic process for preparing methyl tert.-alkyl ether which comprises the steps of
    (a) contacting and reacting in a reaction zone and in the liquid phase a reaction mixture formed by combining a stream consisting essentially of hydrocarbons having from 4 to 5 carbon atoms and containing at least some proportion of an isoalkylene having from 4 to 5 carbon atoms with methanol to form a reaction product comprising methyl tert.-alkyl ether, at least 50 ppm (w) unreacted methanol, unreacted $C_4$-$C_5$ hydrocarbons and at least 5 ppm (w) dimethyl ether;
    (b) isolating at least 99 percent (v) of the methyl tert.-alkyl ether from the reaction product;
    (c) treating the residual portion of the reaction product containing both dimethyl ether and methanol by passing said residual portion through a first adsorption zone containing an adsorbent for both methanol and dimethyl ether whereby at least 95 weight percent of the methanol present is adsorbed and the weight ratio of adsorbed dimethyl ether to adsorbed methanol is at least 0.05 and a substantially methanol-free effluent is obtained which comprises non-adsorbed $C_4$-$C_5$ hydrocarbons and dimethyl ether;
    (d) passing the effluent from step (c) through a second adsorption zone containing a selective adsorbent for dimethyl ether and recovering a hydrocarbon effluent;
    (e) periodically regenerating the first adsorption zone by passing therethrough a purge fluid, and recycling the desorbed methanol and dimethyl ether to the said reaction zone;
    (f) repeating the process of step (a) to produce additional methyl tert.-alkyl ether and a reduced proportion of dimethyl ether with respect to the initial reaction in said reaction zone.

2. Process according to claim 1 wherein in step (d) the weight ratio of adsorbed dimethyl ether to adsorbed methanol is at least 0.10 and less than 0.50.

3. Process according to claim 1 wherein the first adsorption zone is a compound fixed bed comprising silica gel and zeolite 13X.

4. Process according to claim 1 wherein the isoalkylene reacted with methanol is isobutylene.

5. Process according to claim 1 wherein the regeneration of the first adsorption zone in step (e) is carried out using a $C_4$-$C_5$ hydrocarbon stream of essentially the same composition as the hydrocarbon stream fed to the reactor in step (a) in the liquid phase.

6. Process according to claim 5 wherein the regeneration of the first adsorption zone is carried out using the hydrocarbon stream in the liquid phase.

* * * * *